United States Patent [19]

Van der Knaap

[11] Patent Number: Plant 6,343

[45] Date of Patent: Oct. 18, 1988

[54] CHRYSANTHEMUM PLANT NAMED GRETA VERHAGEN

[75] Inventor: Jacques C. M. Van der Knaap, De Lier, Netherlands

[73] Assignee: Fides Beheer B.V., De Lier, Netherlands

[21] Appl. No.: 933,088

[22] Filed: Nov. 20, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A chrysanthemum plant named Greta Verhagen particularly characterized by its single flower type and flat ray floret and capitulum form; yellow ray florets; relatively dark immature disc florets which mature in color to the color of the ray florets; numerous flowers along each stem, and by its disease resistance.

1 Drawing Sheet

The present invention comprises a new and distinct cultivar of Chrysanthemum, botanically known as *Chrysanthemum morifolium,* Ramat., and referred to by the cultivar name Greta Verhagen.

Greta Verhagen is a product of a planned breeding program which had the objective of creating new chrysanthemum cultivars for use in spray mum programs having early response, substantial flowering along the stem, yellow flowers with green centers, and the ability to produce commercially acceptable quality in year around cut mum programs. Such traits in combination were not present or needed improvement in previously available commercial cultivars.

Greta Vehagen was originated from a hybridization made by applicant in a controlled breeding program in De Lier, The Netherlands in 1981. The female parent was the cultivar Citation. The male parent of Greta Verhagen was the cultivar Frost.

Greta Verhagen was discovered and selected as one flowering plant within the progeny of the stated parentage by applicant in a controlled environment in De Lier, The Netherlands.

The first act of asexual reproduction of Greta Verhagen was accomplished when vegetative cuttings were taken from the initial selection in July of 1981 in a controlled environment in De Lier, The Netherlands by a technician working under formulations established and supervised by applicant. Horticultural examination of selected units initiated in April of 1982 has demonstrated that the combination of characteristics as herein disclosed for Greta Verhagen are firmly fixed and are retained through successive generations of asexual reproduction.

Greta Verhagen has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial practice.

The following traits have been repeatedly observed and are determined to be basic characteristics of Greta Verhagen, which, in combination, distinguish this chrysanthemum as a new and distinct cultivar:

1. Flat capitulum form.
2. Single flower type.

3. Yellow ray florets.
4. Immature disc florets are a relatively dark, intense green.
5. Diameter across the face of the capitulum of 50–60 mm.
6. Many flowers along the stem.
7. Tolerance to white rust disease.

Of the many commercial cultivars known to the present inventor, the most similar in comparison to Greta Verhagen is the cultivar Carella. In comparison to Carella, Greta Verhagen has flat ray florets and an unusually green disc floret center for immature and partially mature flowers. The growth habit and response periods of Greta Verhagen are similar to those same characteristics of Carella.

The accompanying color photographic drawing shows typical inflorescence and foliage characteristics of Greta Verhagen, with colors being as nearly true as possible with illustrations of this type.

In the following description, color references are made to the Royal Horticultural Society Colour Chart. The color values were determined between 11:00 a.m. and 12:00 noon in September of 1986 under natural daylight at De Lier, The Netherlands.

Classification:

*Botanical.*—*Chrysanthemum morifolium,* Ramat., cv. Greta Verhagen

*Commercial.*—Cut daisy spray.

INFLORESCENCE

A. Capitulum:

*Form.*—Flat.

*Type.*—Daisy.

*Diameter across face.*—50–60 mm.

B. Corolla of ray florets:

*Color (general tonality from a distance of three meters).*—Yellow.

*Color (upper surface)*—6A.

*Color (under surface).*—10A.

C. Corolla of disc florets:

*Color (mature).*—6C–D.

*Color )immature).*—137A.

D. Reproductive organs:

*Androecium.*—Present only in disc florets; numerous.

*Gynoecium.*—Present in both ray and disc florets; numerous.

PLANT

A. General appearance:
*Height.*—90 cm.

B. Foliage:
*Color (upper surface).*—137A.
*Color (under surface).*—137B.
*Shape.*—Deeply serrated.

I claim:

1. A new and distinct cultivar of chrysanthemum plant named Greta Verhagen, as described and illustrated, and particularly characterized by its single flower type and flat ray floret and capitulum form; yellow ray florets; relatively dark immature disc florets which mature in color to the color of the ray florets; numerous flowers along each stem, and by its disease resistance.

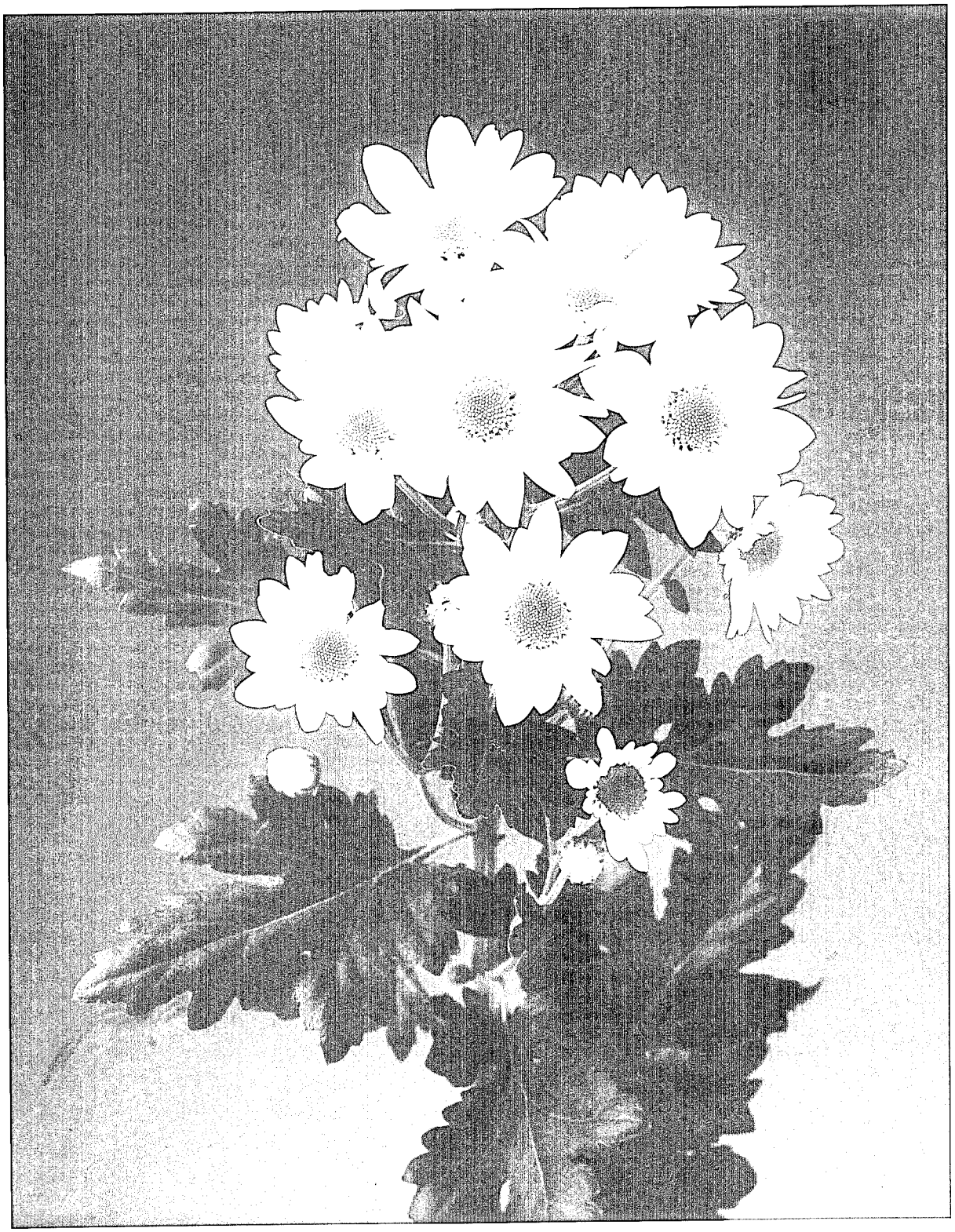

* * * * *